(12) United States Patent
Schunicht et al.

(10) Patent No.: US 7,465,438 B2
(45) Date of Patent: Dec. 16, 2008

(54) SOLUBILIZING AGENTS/SOLVENTS FOR ORGANIC UV FILTERS

(75) Inventors: Christoph Schunicht, Essen (DE); Burghard Gruning, Essen (DE); Pawel Grzebyk, Oberhausen (DE); Klaus Jenni, Essen (DE)

(73) Assignee: Goldschmidt GmbH, Essen (DE)

( * ) Notice: Subject to any disclaimer, the term of this patent is extended or adjusted under 35 U.S.C. 154(b) by 498 days.

(21) Appl. No.: 11/105,837

(22) Filed: Apr. 14, 2005

(65) Prior Publication Data

US 2005/0232877 A1 Oct. 20, 2005

(30) Foreign Application Priority Data

Apr. 14, 2004 (DE) ........................ 10 2004 018 510

(51) Int. Cl.
*A61K 8/00* (2006.01)
*A61K 8/18* (2006.01)
*A61K 8/02* (2006.01)
*A61K 31/44* (2006.01)
*A61Q 17/04* (2006.01)

(52) U.S. Cl. ........................ 424/59; 424/401; 514/292

(58) Field of Classification Search ........................ None
See application file for complete search history.

(56) References Cited

U.S. PATENT DOCUMENTS 5,783,173 A * 7/1998 Bonda et al. .................. 424/59
7,166,275 B2 * 1/2007 Bertz et al. .................... 424/59

OTHER PUBLICATIONS

Pathak, Madhu, "Sunscreens: Topical and Systemic Approaches for Protection of Human Skin Against Harmful Effects of Solar Radiation", Continuing Medical Education Series, J. Am. Acad. Dermat, 7: 3 (Sep. 1982) p. 285,291).

* cited by examiner

*Primary Examiner*—Sreeni Padmanabhan
*Assistant Examiner*—Luke E Karpinski
(74) *Attorney, Agent, or Firm*—Scully, Scott, Murphy & Presser, P.C.

(57) ABSTRACT

The invention relates to the use of compounds of the general formula (I)

$$\left[(R)_a\text{-Ph-}(H_2C)_c\text{-}(X)_d\text{-}\left(CH_2\text{-}\underset{R^1}{\underset{|}{HC}}\text{-}\right)_e\text{-}(A)_f\right]_m$$

$$\left[\left(\underset{R^2}{\underset{|}{CH}}\text{-}H_2C\right)_g\text{-}(Y)_h\text{-}(CH_2)_k\text{-Ph-}(R^1)_b\right]_n$$

wherein
R, R'=H, $C_{1-5}$-hydrocarbon radical, —O—$C_{1-5}$-oxyhydrocarbon radical and are identical or different,
$R^1$, $R^2$, $R^3$=H, $C_{1-5}$-hydrocarbon radical and are identical or different,
X, Y=—O—; —O—C(O)—; —(O)C—O— and are identical or different,
A=$A_\alpha$=—O—C(O)—O—; $A_\beta$=$R^4$—$CH_2C(CH_2\text{—})_3$, $A_\gamma$=—C(H)-isopropyl, $R^4$=$R^4_\delta$=—$CH_3$; $R^4_\epsilon$=—[$CH_2$—$CH(R^1)]_e$—$(Y)_d$—$(CH_2)_c$-Ph$(R)_a$,
a, b=1 to 5 and are identical or different,
c, k=0 to 5 and are identical or different,
d, h=0 or 1 and are identical or different,
e, g=0 or 1 and are identical or different,
f=0 or 1,
m=1 to 3,
n=0 or 1,
as solubilizing agents/solvents for dissolving organic UV filters.

15 Claims, No Drawings

SOLUBILIZING AGENTS/SOLVENTS FOR ORGANIC UV FILTERS

FIELD OF THE INVENTION

The present invention relates to improved solubilizing agents/solvents for organic ultraviolet (UV) filters and the use of these materials in cosmetically acceptable products for improved protection against UV radiation as well as cosmetic formulations which can better protect the user against UV radiation.

BACKGROUND OF THE INVENTION

It has been known for a long time that certain amounts of ultraviolet content, in particular, that which is associated with natural and artificial light sources (UV-A 320 to 390 nm; UV-B 280 to 320 nm; UV-C 100 or 200 to 280 nm), lead to damage to the human skin.

UV-A radiation chiefly has the effect of ageing of the skin (thinning of the epidermis and degeneration of connective tissue, and pigment disorders), while UV-B and UV-C lead to sunburn and skin cancer.

Leisure activities which have changed in recent years with longer periods in the open air and, in particular, extensive sunbathing to achieve the "healthy tan" have, however, against the background of medical findings and the awareness of the lack of natural protection mechanisms of the skin by pigment formation and solar acclimatization by thickening of the horny layer, shifted the need for adequate protection against intensive UV radiation. It has been intensified significantly by the discussion of the decrease and thinning of the Antarctic ozone hole and the associated increase in the intensity of UV-A and UV-B radiation on the earth's surface.

This becomes clear from the increasing turnovers in recent years of products with high sun protection factors (SPFs). These are primarily still the conventional sun protection formulations (sun milk, sun oil) with the primary intended use of sunbathing, but increasingly also the so-called care products for the face, body and hair, such as day and night creams, conditioners, lotions, (hydro, lipo) gels, (lip)sticks and sprays, pharmaceutical formulations and to a small extent products of decorative cosmetics, which are predominantly commercially available in the form of oils and liquid, cream-like or ointment/paste-like W/O and O/W emulsions.

As stated above, UV-B radiation can cause tanning and burns, rather than UV-A radiation. Prior art sun protection compositions therefore predominantly comprise only filters which protect against UV-B radiation. Since the effects/side effects of a suntan/sunburn are not immediately and clearly perceptible, the skin is exposed to radiation for significantly longer than would be appropriate.

However, the skin is therefore predominantly exposed unprotected to UV-A radiation. The problem is thus that UV-A radiation penetrates into the skin and causes long-term damage, even though it does not cause immediately detectable actions.

Medical findings in recent years have clearly demonstrated that not only UV-B radiation but also UV-A radiation is harmful to the skin. It has been demonstrated that enzymes which repair cells damaged by UV-B radiation are inhibited in their activity and thus UV-A radiation indirectly promotes skin cancer. By deeper depth of penetration, UV-A radiation can even cause changes in the blood vessels.

Moreover, UV-A radiation is the origin of most photodermatoses, such as sun allergies: small red blisters which appear on the arms and neckline during first exposure to sun and are accompanied by severe itching. In the long term, with abuse of the sun, they can cause skin cancer.

UV-A rays are, therefore, almost more dangerous than UV-B rays, since they issue no alarm signal, such as sunburn. When their damage is noticed, it is already too late.

With increased exposure to the sun, an increase in various infectious skin diseases, such as mycoses or herpes, has been found.

This increase is based on the ability of the UV rays to weaken the immune system of the skin, thus to reduce its capacity to react and to reduce the defense against causes of infections, such as, for example, herpes virus or skin fungi. It is assumed nowadays that the phenomenon of photoimmunosuppression also plays a significant role in the development of skin cancer.

For sun protection of naked, uncovered skin and hair (bleaching, embrittlement), particularly of the face and lips, sun protection compositions, which ensure adequate and lasting protection over the entire harmful UV spectrum, are therefore in demand.

Such broad-band sun protection compositions can comprise a combination of corresponding organic UV-A and UV-B filters.

By these there are to be understood organic substances which are liquid or crystalline at room temperature and which are capable of absorbing ultraviolet rays and of releasing the energy absorbed again in the form of longer-wavelength radiation, e.g., heat. To establish a sufficiently high sun protection factor, however, correspondingly high contents of these filters must be used.

During lasting exposure of the skin to sun, the protection should be renewed at regular intervals of approximately one to four hours. The same applies during sports activity, in order to compensate the decrease in protection, i.e., loss of the filter substances by bathing, perspiration or mechanical abrasion by clothing or hand towels.

Only the regular use of light protection products with a high SPF and a broad absorption spectrum both against UVA and against UVB rays allows an effective protection. Furthermore, because of the increased incident solar radiation in some regions, sun protection formulations, which have a greatly increased light protection factor, are increasingly required.

The light protection factor LPF or also SPF is a coefficient that expresses the ability of a product to prevent sunburn by the sun. Light protection with a factor of 60 therefore protects against the occurrence of sunburn for twice as long as a product with factor 30, and correspondingly 3 times as long as a product with factor 20.

These higher light protection factors are in most cases generated by an increase in the concentration of UV filter substances in the formulation.

Since 1995, light protection factors have been measured by the same international standard (COLIPA), which allows comparison between the various manufacturers.

Given these frequent uses over large areas, it is not ruled out that the high-dosed filters (approximately 3 to 30 wt. % of the formulation) are applied to the skin in gram quantities.

However, these amounts of filter substances must have been dissolved and incorporated into the formulation in a homogeneous and stable manner.

Oily components that have a good dissolving power for the filter substances are often used to dissolve these substances. Certain ester oils, inter alia, are thus also employed. Aliphatic benzoic acid esters are a class of compounds used here. A typical representative of this class of compounds is the compound Tegosoft® TN ($C_{12-15}$-alkyl benzoate), which has been employed particularly frequently as a solvent for UV filter substances.

Nevertheless, the dissolving power of the established compounds often is not sufficient to dissolve relatively large amounts of UV filter substances.

This increase in concentration is therefore problematic in practice, or under certain circumstances even impossible.

Incompletely dissolved UV filter contents in the end product can put the stated SPF in doubt under certain circumstances. Even if the solution properties of the sun protection filter initially still exist in their entirety, under storage conditions, which are extreme but relevant in practice, precipitation of the filters and, therefore, a loss in action can nevertheless occur.

In view of the above discussion, there is a need to overcome these disadvantages and to provide cosmetic formulations which have a particularly high dissolving power for UV filters.

SUMMARY OF THE INVENTION

The present invention obviates the problems mentioned above by utilizing new solubilizing agents/solvents for dissolving organic UV filters.

The inventive compounds are distinguished by their particularly high dissolving power for organic crystalline UV-A and UV-B filters. At the same time, the inventive compounds have a comparatively high content of aromatic groups in the molecule.

It is now known from the prior art that the introduction of aromatic groups, such as, e.g., phenyl radicals, into a molecular skeleton often results in a significant increase in the melting point, so that the compounds are solid at room temperature. In some cases, compounds with a high aromatic content have melting points of greater than 100° C., which means that incorporation into cosmetic formulations is made very difficult. Surprisingly, in spite of their comparatively high content of aromatic groups, the compounds according to the invention are liquid at room temperature or have a low melting point of less than 70° C.

Due to their low melting point, the substances according to the invention can be incorporated into cosmetic formulations at low processing temperatures below the boiling point of water which are preferred in the cosmetics industry. The compounds according to the invention, which are solid at room temperature, can also advantageously be employed in combination with liquid compounds, therefore it is possible for liquid mixtures to be obtained.

These properties make the compounds according to the invention suitable ingredients of cosmetic formulations.

The present invention therefore relates to a method for dissolving organic UV filter which comprises the utilization of compounds of the general formula (I)

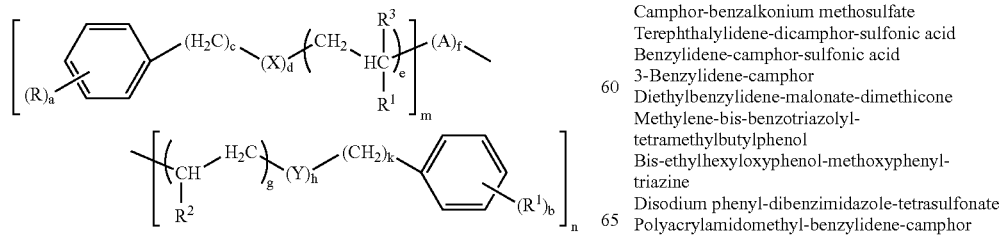

wherein
R, R' are the same or different and are H, a $C_{1-5}$-hydrocarbon radical, or a —O—$C_{1-5}$-oxhydrocarbon radical,
$R^1$, $R^2$, $R^3$ are the same or different and are H, or a $C_{1-5}$-hydrocarbon radical,
X, Y are the same or different and are —O—; —O—C(O)—; or —(O)C—O,
A is $A_\alpha$ which is —O—C(O)—O—; $A_\beta$ which is $R^4$—$CH_2C(CH_2$—$)_3$—, or $A_\gamma$ which is —C(H)— isopropyl, where $R^4$=$R^4{}_\delta$=—$CH_3$; $R^4{}_\epsilon$=—[$CH_2$—CH($R^1$)]$_e$ —(Y)$_d$—($CH_2$)$_c$-Ph(R)$_a$,
a, b are the same or different and are 1 to 5,
c, k are the same or different and are 0 to 5,
d, h are the same or different and are 0 or 1,
e, g are the same or different and are 0 or 1,
f is 0 or 1,
m is 1 to 3, and
n=0 or 1, as solubilizing agents/solvents for dissolving said organic UV filters.

The present invention also relates to the use of these solubilizing agents/solvents for dissolving organic UV filters for the preparation of cosmetic formulations.

The present invention furthermore relates to cosmetic formulations with improved sun protection factor comprising organic UV filters dissolved in the improved solubilizing agents/solvents.

DETAILED DESCRIPTION OF THE INVENTION

As stated above, the present invention provides a method in which organic UV filters can be dissolved using the compound described above by formula (I) as well as cosmetic formulations that include the same.

Organic UV filters that can be co-used according to the invention are, for example, the compounds listed below (FDA registration name in parentheses):

| Filter | FDA registration name |
|---|---|
| Ethylhexyl methoxycinnamate | Octinoxate |
| Benzophenone-3 | Oxybenzone |
| | Octocrylene |
| Butyl-methoxydibenzoylmethane | Avobenzone |
| Ethylhexyl salicylate | Octisalate |
| Homobornyl salicylate | Homosalate |
| Phenylbenzimidazole-sulfonic acid | Phenylbenzimidazole-sulfonic acid |
| Benzophenone-4,-5 | Sulisobenzone |
| Ethylhexyl dimethyl-PABA | Padimate O |
| 4-Aminobenzoic acid | PABA |
| Butyl methoxycinnamate | Cinoxate |
| Benzophenone-8 | Dioxybenzone |
| Menthyl anthranilate | Menthyl anthranilate |
| 4-Methylbenzylidene-camphor | |
| Ethylhexyl-triazone | |
| PEG-25 PABA | |
| Isoamyl p-methoxycinnamate | |
| Diethylhexyl-butamido-triazone | |
| Drometrizole-trisiloxane | |
| Camphor-benzalkonium methosulfate | |
| Terephthalylidene-dicamphor-sulfonic acid | |
| Benzylidene-camphor-sulfonic acid | |
| 3-Benzylidene-camphor | |
| Diethylbenzylidene-malonate-dimethicone | |
| Methylene-bis-benzotriazolyl-tetramethylbutylphenol | |
| Bis-ethylhexyloxyphenol-methoxyphenyl-triazine | |
| Disodium phenyl-dibenzimidazole-tetrasulfonate | |
| Polyacrylamidomethyl-benzylidene-camphor | |

The most widely used chemical sun protection compositions comprise, for example, p-aminobenzoic acid (PABA), PABA esters (glyceryl PABA, amyldimethyl PABA and octyldimethyl PABA), benzophenone derivatives (oxybenzone und sulisobenzone), cinnamates (octyl methoxycinnamate and cinoxate), salicylates (homobornyl ethyl salicylate) and anthranilates (see, for example, Pathak Madhu, "Sunscreens: Topical and Systemic Approaches for Protection of Human Skin Against Harmful Effects of Solar Radiation", Continuing Medical Education Series, J. Am. Acad. Dermat, 7: 3 (September 1982) p. 285, 291).

Three representative UV-A or UV-B filters were chosen as representatives for testing the dissolving power for crystalline UV filters in the substances described. These are benzophenone-3 (2-hydroxy-4methoxy-benzophenone) und butylmethoxydibenzoylmethane as two UV-A filters and methylbenzylidene-camphor as a UV-B filter.

The dissolving power of conventional ester oils for these three compounds is not satisfactory in most cases. A compound with an above-average dissolving power for UV filter substances is Tegosoft® TN already mentioned, which is therefore also widely established as an ingredient for sun protection formulations.

It has now been found that the dissolving power of the compounds according to the invention not only is comparable to that of Tegosoft® TN, but in many cases also significantly exceeds this.

The required cosmetic formulations with a particularly high dissolving power for UV filters can be readily realized in this manner.

Suitable carriers for the preparation of such sun protection formulations include lanolin, glyceryl stearate, cocoa butter, sorbitan sesquioleate, propylene glycol, isopropyl myristate, petrolatum and acrylic polymers. Mixtures of two or more of these substances can furthermore be used. These substances are known in the prior art as "dermatologically suitable", i.e., they cause or promote no adverse reactions on the skin of the user.

The amount of the carrier must merely be sufficient to achieve a uniform distribution on application to the skin, so that adequate covering of the skin with the UV-absorbing material is ensured.

The oily formulations described above, by themselves or in the form of water-in-oil (W/O) emulsions, can be incorporated into topical sun protection compositions, and furthermore introduced into diverse cosmetic products, such as, for example, lipstick, eye shadow, make-up, moisturizing cream, rouge and further care products, in order to form cosmetics which protect the user's skin underneath against the harmful actions of UV radiation. These materials can be mixed with the cosmetic base composition by known mixing methods.

Further constituents of cosmetic formulations which comprise the compounds of the invention maybe so-called auxiliaries. These auxiliaries are well-known in the prior art and are added in order to fulfill their own functions. The preferred auxiliaries include substances such as thickeners, softeners, superfatting agents, agents for water resistance, emollients, wetting agents and surface-active substances, as well as preservatives, antifoams, perfumes and mixtures thereof or any desired further compatible ingredients which are conventionally used in cosmetics.

The compounds according to the invention are to be obtained by a simple route by esterification of suitable substituted carboxylic acids with the correspondingly suitable alcohols or by transesterification of carboxylic acid esters with suitable alcohols.

In this procedure, mono- and dicarboxylic acids or their esters are reacted with alcohols with aromatic substituents, or carboxylic acids with aromatic substituents or their esters are reacted with branched and unbranched, optionally also aromatic mono- and polyalcohols.

Alternatively, instead of the carboxylic acid esters organic carbonates, such as diethyl carbonate, can also be used. The preparation is carried out by the conventional procedures known from the literature for esterification or transesterification reactions.

The following examples are provided to illustrate the present invention and to demonstrate that the inventive compounds can be used as a solubilizing/solvent for dissolving organic UV filters.

EXAMPLE 1

Preparation of Compound 1:

379.9 g of the alcohol 1-phenoxy-2-propanol were initially introduced into the reaction vessel together with 320.1 g of benzoic acid, 4.2 g of p-toluenesulfonic acid and 0.7 g of hypophosphorous acid. After the mixture had been heated up to 160° C., a vacuum of 400 mbar was applied. After 1.5 h, the vacuum was increased to 200 mbar, and was increased to 30 mbar in further steps. The temperature was then increased to 180° C. After the acid number had reached a value of <15, the mixture was neutralized with potassium hydroxide solution and the product was subjected to a steam treatment. The product was then dried in vacuo at 150° C. After cooling, the product was filtered.

The product was in the form of a slightly yellowish clear liquid with a purity of 90% (GC). The yield was 95%, based on the alcohol.

EXAMPLE 2

Preparation of Compound 2:

129.7 g of the alcohol 1-phenoxy-2-propanol were initially introduced into the reaction vessel together with 50.3 g of diethyl carbonate. After the mixture had been heated up to 110° C., 0.9 g of isopropyl titanate was added. The mixture was now heated slowly up to 240° C. and the ethanol formed was distilled off over a distillation column.

After 4 h, the mixture was cooled to approx. 160° C. and a vacuum of 100 mbar was applied. The vacuum was lowered to 10 mbar in the course of 2.5 h and the further ethanol formed was distilled off until no further distillate was formed. The product was subjected to a steam treatment and then dried at 150° C. in vacuo. After cooling, the product was filtered.

The product was in the form of a clear liquid with a purity of 89% (GC). The yield was 93%, based on the alcohol.

EXAMPLES 3-8

The preparation of compounds 3 to 8 was carried out analogously to Examples 1-2.

The following provides the structural formulas of the compounds produced in Examples 1-8:

Compound 1

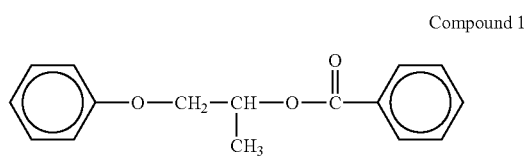

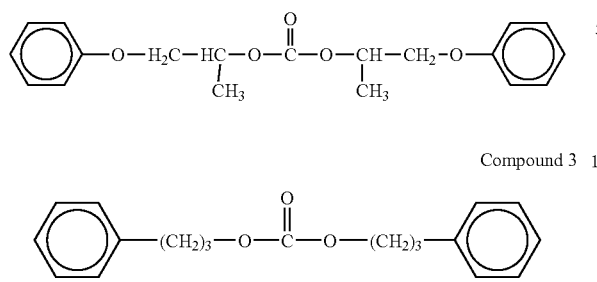

Compound 2

Compound 3

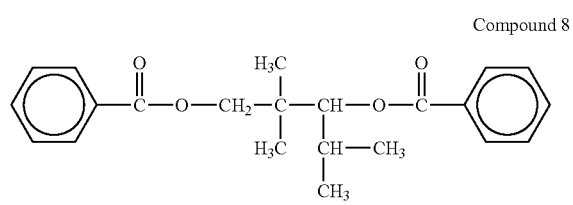

Compound 8

These compounds are defined by the general formula (I) wherein:

TABLE 1

| Compound | R/R' | $R^1/R^2/R^3$ | X/Y | A | a/b | c/k | d/h | e/g | f | m/n |
|---|---|---|---|---|---|---|---|---|---|---|
| 1 | H/H | $CH_3$/—/H | —O—/—O—C(=O)— | — | 5/5 | 0/0 | 1/1 | 1/0 | 0 | 1/1 |
| 2 | H/H | $CH_3/CH_3$/H | —O—/—O— | $A_\alpha$ | 5/5 | 0/0 | 1/1 | 1/1 | 1 | 1/1 |
| 3 | H/H | — | — | $A_\alpha$ | 5/5 | 3/3 | 0/0 | 0/0 | 1 | 1/1 |
| 4 | H/H | H/H/H | —O—C(=O)—/—C(=O)—O— | — | 5/5 | 3/3 | 1/1 | 1/1 | 0 | 1/1 |
| 5 | H/H | — | — | $A_\alpha$ | 5/5 | 1/1 | 0/0 | 0/0 | 1 | 1/1 |
| 6 | H/— | — | —C(=O)—O—/— | $A_\beta$ where $R^4 = R4_\delta$ | 5/— | 0/— | 1/— | 0/— | 1 | 3/0 |
| 7 | H/— | — | —C(=O)—O—/—O—C(=O)— | $A_\beta$ where $R^4 = R4_\epsilon$ | 5/— | 0/— | 1/— | 0/— | 1 | 3/0 |
| 8 | H/H | $CH_3$/—/$CH_3$ | —C(=O)—O—/—O—C(=O)— | $A\gamma$ | 5/5 | 0/0 | 1/1 | 1/0 | 1 | 1/1 |

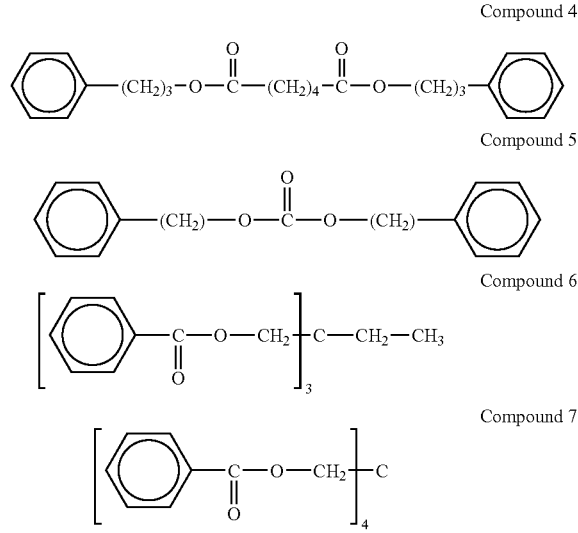

Compound 4

Compound 5

Compound 6

Compound 7

EXAMPLE 9

Test for the dissolving power of crystalline UV filters:

Three representative crystalline UV-A or UV-B filters were chosen as representatives for determination of the solubility of UV filter substances. These are:

Benzophenone-3(=2-hydroxy-4-methoxy-benzophenone) (UV-A filter)
4-Methylbenzylidene-camphor (UV-B filter)
Butyl-methoxy-dibenzoylmethane (UV-A filter)

For the determination of the dissolving power of these three UV filter substances, in each case a particular amount (50 g) of one of the compounds according to the invention was initially introduced into the dissolving vessel and temperature-controlled at 22° C. 1 wt. % of a UV filter was added and the mixture was stirred until this amount had dissolved completely and homogeneously. This operation was repeated until the maximum amount of the UV filter which can be dissolved had been exceeded. For complete dissolving, a relatively long stirring time of several hours was often necessary at higher concentrations.

Once the maximum concentration has been roughly determined in this manner, the test was repeated with smaller weights of the UV filter for fine determination of the concentration range around this maximum concentration.

The compound Tegosoft® TN was used as a reference.
Results of the solubility determinations:

| Compound | Benzophenone-3 | 4-Methylbenzylidene-camphor | Butyl-methoxy-dibenzoylmethane |
|---|---|---|---|
| 1 | 31 | 30.7 | 16.5 |
| 2 | 19.7 | 24.3 | 9.5 |
| 3 | 18.5 | 23.5 | 9.0 |
| 4 | 25.0 | 23.9 | 9.5 |
| 5 | 29.3 | 27.0 | 8.8 |
| 8 | 24.5 | 29.4 | 15.6 |
| Tegosoft® TN | 12.7 | 22.0 | 12.1 |

As can be seen from the above values, the dissolving power of the compounds according to the invention was significantly better than the dissolving power of Tegosoft® TN in many cases.

EXAMPLE 10

Examples of cosmetic formulations:

The compounds according to the invention were employed as a constituent of cosmetic formulations. A water-in-oil (W/O) and an oil-in-water (O/W) cream were chosen for this by way of example.
A) Standard Test Recipe W/O (W/O Sun Cream)
Preparation:
Batch size: in each case 100 g
1. Melt the constituents of phase A in a glass beaker at 80° C. and transfer to a glass beaker.
2. Bring the constituents of phase A to a controlled temperature of 80° C. in a drying cabinet.
3. Dissolve the constituents of phase B in a glass beaker.
4. Stir in phase B slowly while stirring with an MIG stirrer (500 rpm) and then homogenize for 3 minutes at 1,400 rpm.
Standard Test Recipe W/O 1:

With Tegosoft® TN as the solvent for the UV filter benzophenone-3 (12% based on the mixture with Tegosoft® TN).

| | Standard test recipe W/O | |
|---|---|---|
| | | % |
| A | ISOLAN ® PDI | 3.0 |
| | Castor Wax | 0.5 |
| | Microwax W 80 | 0.5 |
| | Tegosoft ® TN | 22.85 |
| | Benzophenone-3 | 3.15 |
| | (Total oily phase 30%) | |
| B | MgSO$_4$*7H$_2$O | 1.0 |
| | Water | 68.95 |
| | Bronopol | 0.05 |

Standard Test Recipe W/O 2:

With compound 1 as the solvent for the UV filter benzophenone-3 (12% based on the mixture with compound 1).

This standard test recipe served to check whether the recipe constituent Tegosoft® TN can be replaced without problems by a comparable amount of compound 1 in standard test recipe W/O 1 without fundamentally changing the properties of the standard test recipe.

| | Standard test recipe W/O | |
|---|---|---|
| | | % |
| A | ISOLAN ® PDI | 3.0 |
| | Castor Wax | 0.5 |
| | Microwax W 80 | 0.5 |
| | Compound 1 | 22.85 |
| | Benzophenone-3 | 3.15 |
| | (Total oily phase 30%) | |
| B | NaCl | 1.0 |
| | Water | 68.95 |
| | Bronopol | 0.05 |

Standard Test Recipe W/O 3:

With compound 1 as the solvent for the UV filter benzophenone-3 (24% based on the mixture with compound 1).

This standard test recipe served to check whether the content of the UV filter benzophenone-3 can be significantly increased in the standard test recipe compared with the standard test recipe W/O 2 without fundamentally changing the properties of the standard test recipe.

| | Standard test recipe W/O | |
|---|---|---|
| | | % |
| A | ISOLAN ® PDI | 3.0 |
| | Castor Wax | 0.5 |
| | Microwax W 80 | 0.5 |
| | Compound 1 | 19.76 |
| | Benzophenone-3 | 6.24 |
| | (Total oily phase 30%) | |
| B | NaCl | 1.0 |
| | Water | 68.95 |
| | Bronopol | 0.05 |

As has been seen from the preparation and checking of the abovementioned recipes, it was possible both for the recipe constituent Tegosoft® TN to be replaced without problems by a comparable amount of compound 1 in standard test recipe W/O 1 and for the content of the UV filter benzophenone-3 in the standard test recipe to be increased significantly, without fundamentally changing the properties of the standard test recipe.
B) Standard Test Recipe O/W (O/W Sun Cream)
Preparation:
Batch size: in each case 100 g
1. Heat the constituents of phase A to 80° C. in a 400 ml glass beaker.
2. Heat the constituents of phase B to 80° C. in a 250 ml glass beaker.
3. Add phase B to phase A and then homogenize with an ESG bar for 2 minutes.
4. Cool to 50 to 60° C. in a water bath, while stirring, add phase C and homogenize again for 1 minute.
5. Cool to <30° C. in a water bath, while stirring.
Standard Test Recipe O/W 1:

With Tegosoft® TN as the solvent for the UV filter methyl-benzylidene-camphor (20% based on the mixture with Tegosoft® TN).

| Standard test recipe O/W | | | |
|---|---|---|---|
| | | | % |
| A | TEGO ® Care 215 | | 2.5 |
| | TEGIN ® M | | 1.0 |
| | TEGO ® Alkanol 18 | | 2.0 |
| | TEGOSOFT ® TN | | 11.6 |
| | Methylbenzylidene-camphor | | 2.9 |
| | (Total oily phase 20%) | | |
| B | Glycerol | | 3.0 |
| | Water | | 76.5 |
| | CA 24 ® | | 0.1 |
| C | Keltrol F ® | | 0.4 |

Standard Test Recipe O/W 2:

With compound 1 as the solvent for the UV filter methylbenzylidene-camphor (20% based on the mixture with compound 1). This standard test recipe served to check whether the recipe constituent Tegosoft® TN can be replaced without problems by a comparable amount of compound 1 in standard test recipe O/W 1 without fundamentally changing the properties of the standard test recipe.

| Standard test recipe O/W | | | |
|---|---|---|---|
| | | | % |
| A | TEGO ® Care 215 | | 2.5 |
| | TEGIN ® M | | 1.0 |
| | TEGO ® Alkanol 18 | | 2.0 |
| | Compound 1 | | 11.6 |
| | Methylbenzylidene-camphor | | 2.9 |
| | (Total oily phase 20%) | | |
| B | Glycerol | | 3.0 |
| | Water | | 76.5 |
| | CA 24 ® | | 0.1 |
| C | Keltrol F ® | | 0.4 |

Standard Test Recipe O/W 3:

With compound 1 as the solvent for the UV filter methylbenzylidene-camphor (30% based on the mixture with compound 1). This standard test recipe served to check whether the content of the UV filter methylbenzylidene-camphor can be significantly increased in the standard test recipe compared with standard test recipe W/O 2 without fundamentally changing the properties of the standard test recipe.

| Standard test recipe O/W | | | |
|---|---|---|---|
| | | | % |
| A | TEGO ® Care 215 | | 2.5 |
| | TEGIN ® M | | 1.0 |
| | TEGO ® Alkanol 18 | | 2.0 |
| | Compound 1 | | 10.15 |
| | Methylbenzylidene-camphor | | 4.35 |
| | (Total oily phase 20%) | | |
| B | Glycerol | | 3.0 |
| | Water | | 76.5 |
| | CA 24 ® | | 0.1 |
| C | Keltrol F ® | | 0.4 |

As has been seen from the preparation and checking of the abovementioned recipes, it was possible both for the recipe constituent Tegosoft® TN to be replaced without problems by a comparable amount of compound 1 in standard test recipe O/W 1 and for the content of the UV filter methylbenzylidene-camphor in the standard test recipe to be increased significantly, without fundamentally changing the properties of the standard test recipe.

By the preparation of the six recipes listed above it has thus been possible to demonstrate that it was possible to increase the amount of UV filter in the recipes by virtually 100% by using the compounds according to the invention.

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A method of dissolving organic UV filters comprising:
contacting an organic UV filter with at least one compound of the general formula

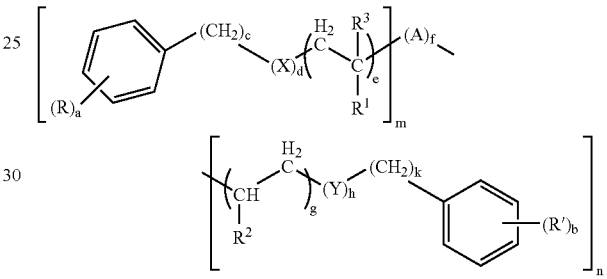

wherein
R, R' are the same or different and are H, a $C_{1-5}$-hydrocarbon radical, or a —O—$C_{1-5}$-oxyhydrocarbon radical,
$R^1$, $R^2$, $R^3$ are the same or different and are H, or a $C_{1-5}$-hydrocarbon radical,
X, Y are the same or different and are —O—; —O—C(O)—; or —(O)C—O—,
A is $A_\alpha$ which is —O—C(O)—O—; $A_\beta$ which is $R^4$—$CH_2C(CH_2$—$)_3$, or $A_\gamma$ which is —C(H)-isopropyl, where $R^4$=$R^4_\epsilon$=—[$CH_2$—$CH(R^1)]_e$—$(Y)_d$—$(CH_2)_c$-Ph$(R)_a$,
a, b are the same or different and are 1 to 5,
c, k are the same or different and are 0 to 5,
d, h are 1,
e, g are the same or different and are 0 or 1,
f is 0 or 1,
m is 1 to 3, and
n is 1.

2. The method of claim 1, wherein
R, R'=both H,
$R^1$, $R^2$, $R^3$=—$CH_3$,
X, Y=both —O—,
A=—O—C(O)—O—,
a, b=both 5 or 0,
c, k=0 or 1 or 3 and are identical or different,
d, h=0 or 1 and are identical or different,
e, g=0 or 1 and are identical or different,
f=1,
m=1, and
n=1.

3. The method of claim 1, wherein
R=H

X, Y=—O—C(O)—; —(O)C—O— and are identical or different;
A=A$_\beta$=R$^4$—CH$_2$—C(CH$_2$—)$_3$, R$^4$=R$^4_\epsilon$=—[CH$_2$—CH(R$^1$)]$_e$—(Y)$_d$—(CH$_2$)$_c$-Ph(R)$_a$,
a, b=5 or 0 and are identical or different,
c, k=0,
d, h=1 or 0 and are identical or different,
e, g=0,
f=1,
m=3,
n=0.

4. The method of claim 1, wherein
R, R'=H,
R$^1$, R$^2$, R$^3$=H, or CH$_3$ and are identical or different,
X, Y=—O—; —O—C(O)—; —(O)C—O— and are identical or different,
a, b=5,
c, k=0 or 3 and are identical or different
d, h=1,
e, g=0 or 1 and are identical or different,
f=0,
m=1,
n=1.

5. The method of claim 1, wherein
R, R'=H,
R$^1$, R$^2$, R$^3$=H, or CH$_3$ and are identical or different,
X, Y=—O—C(O)— or —(O)C—O— and are identical or different
A=A$_\gamma$=—C(H)-isopropyl,
a, b=5,
c, k=0,
d, h=1,
e, g=0 or 1 and are identical or different,
f=1,
m=1,
n=1.

6. A method of preparing a cosmetic formulation comprising:
contacting an organic UV filter with at least one compound of the following formula

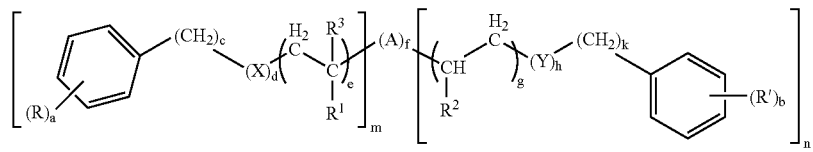

wherein
R, R' are the same or different and are H, a C$_{1-5}$-hydrocarbon radical, or a —O—C$_{1-5}$-oxyhydrocarbon radical,
R$^1$, R$^2$, R$^3$ are the same or different and are H, or a C$_{1-5}$-hydrocarbon radical,
X, Y are the same or different and are —O—; —O—C(O)—; or —(O)C—O—,
A is A$_\alpha$ which is —O—C(O)—O—; A$_\beta$ which is R$^4$—CH$_2$C(CH$_2$—)$_3$, or A$_\gamma$ which is —C(H)-isopropyl, where R$^4$=R$^4_\epsilon$=—[CH$_2$—CH(R$^1$)]$_e$—(Y)$_d$—(CH$_2$)$_c$-Ph(R)$_a$,
a, b are the same or different and are 1 to 5,
c, k are the same or different and are 0 to 5,
d, h are 1,
e, g are the same or different and are 0 or 1,
f is 0 or 1,
m is 1 to 3, and
n is 1.

7. The method of claim 6, wherein
R, R'=both H,
R$^1$, R$^2$, R$^3$=—CH$_3$,
X, Y=both —O—,
A=—O—C(O)—O—,
a, b=both 5 or 0,
c, k=0 or 1 or 3 and are identical or different,
d, h=0 or 1 and are identical or different,
e, g=0 or 1 and are identical or different,
f=1,
m=1, and
n=1.

8. The method of claim 6, wherein
R=H
X, Y=—O—C(O)—; —(O)C—O— and are identical or different;
A=A$_\beta$=R$^4$—CH$_2$—C(CH$_2$—)$_3$, R$^4$=R$^4_\epsilon$=—[CH$_2$—CH(R$^1$)]$_e$—(Y)$_d$—(CH$_2$)$_c$-Ph(R)$_a$,
a, b=5 or 0 and are identical or different,
c, k=0,
d, h=1 or 0 and are identical or different,
e, g=0,
f=1,
m=3,
n=0.

9. The method of claim 6, wherein
R, R'=H,
R$^1$, R$^2$, R$^3$=H, CH$_3$ or 0 and are identical or different,
X, Y=—O—; —O—C(O)—; —(O)C—O— and are identical or different,
a, b=5,
c, k=0 or 3 and are identical or different
d, h=1,
e, g=0 or 1 and are identical or different,
f=0,
m=1,
n=1.

10. The method of claim 6, wherein
R, R'=H,
R$^1$, R$^2$, R$^3$=H, or CH$_3$ and are identical or different,
X, Y=—O—C(O)— or —(O)C—O— and are identical or different
A=A$_\gamma$=—C(H)-isopropyl,
a, b=5,
c, k=0,
d, h=1,
e, g=0 or 1 and are identical or different,
f=1,
m=1,
n=1.

11. A cosmetic formulation comprising an organic UV filter dissolved with at least one compound of the following formula

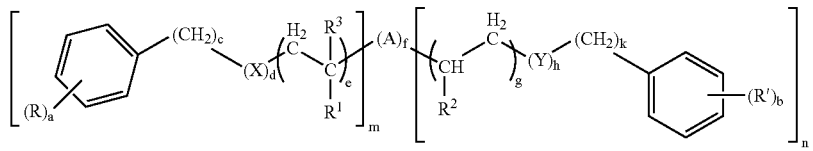

wherein
R, R' are the same or different and are H, a $C_{1-5}$-hydrocarbon radical, or a —O—$C_{1-5}$-oxyhydrocarbon radical,
$R^1$, $R^2$, $R^3$ are the same or different and are H, or a $C_{1-5}$-hydrocarbon radical,
X, Y are the same or different and are —O—; —O—C(O)—; or —(O)C—O—,
A is $A_\alpha$ which is —O—C(O)—O—; $A_\beta$ which is $R^4$—$CH_2C(CH_2—)_3$, or $A_\gamma$ which is —C(H)-isopropyl, where $R^4 = R^4_\epsilon =$ —$[CH_2—CH(R^1)]_e$—$(Y)_d$—$(CH_2)_c$-Ph$(R)_a$,
a, b are the same or different and are 1 to 5,
c, k are the same or different and are 0 to 5,
d, h are 1,
e, g are the same or different and are 0 or 1,
f is 0 or 1,
m is 1 to 3, and
n is 1.

12. The cosmetic formulation of claim 11, wherein
R, R'=both H,
$R^1$, $R^2$, $R^3$=—$CH_3$,
X, Y=both —O—,
A=—O—C(O)—O—,
a, b=both 5 or 0,
c, k=0 or 1 or 3 and are identical or different,
d, h=0 or 1 and are identical or different,
e, g=0 or 1 and are identical or different,
f=1,
m=1, and
n=1.

13. The cosmetic formulation of claim 11, wherein
R=H
X, Y=—O—C(O)—; —(O)C—O— and are identical or different;
A=$A_\beta$=$R^4$—$CH_2$—$C(CH_2—)_3$, $R^4 = R^4_\epsilon =$—$[CH_2—CH(R^1)]_e$—$(Y)_d$—$(CH_2)_c$-Ph$(R)_a$,
a, b=5 or 0 and are identical or different,
c, k=0,
d, h=1 or 0 and are identical or different,
e, g=0,
f=1,
m=3,
n=0.

14. The cosmetic formulation of claim 11, wherein
R, R'=H,
$R^1$, $R^2$, $R^3$=H, or $CH_3$ and are identical or different,
X, Y=—O—; —O—C(O)—; —(O)C—O— and are identical or different,
a, b=5,
c, k=0 or 3 and are identical or different
d, h=1,
e, g=0 or 1 and are identical or different,
f=0,
m=1,
n=1.

15. The cosmetic formulation of claim 11, wherein
R, R'=H,
$R^1$, $R^2$, $R^3$=H, or $CH_3$ and are identical or different,
X, Y=—O—C(O)— or —(O)C—O— and are identical or different
A=$A_\gamma$=—C(H)-isopropyl,
a, b=5,
c, k=0,
d, h=1,
e, g=0 or 1 and are identical or different,
f=1,
m=1,
n=1.

* * * * *